(12) United States Patent
Yamada et al.

(10) Patent No.: US 7,410,066 B2
(45) Date of Patent: Aug. 12, 2008

(54) FILTER FOR SELECTIVELY ELIMINATING LEUKOCYTES

(75) Inventors: Yukihiro Yamada, Oita (JP); Hirofumi Miura, Tokyo (JP)

(73) Assignee: Ashai Kasei Medical Co., Ltd, Tokyo (JP)

( * ) Notice: Subject to any disclaimer, the term of this patent is extended or adjusted under 35 U.S.C. 154(b) by 524 days.

(21) Appl. No.: 10/497,607

(22) PCT Filed: Dec. 2, 2002

(86) PCT No.: PCT/JP02/12597

§ 371 (c)(1), (2), (4) Date: Jan. 6, 2005

(87) PCT Pub. No.: WO03/047655

PCT Pub. Date: Jun. 12, 2003

(65) Prior Publication Data

US 2005/0121386 A1    Jun. 9, 2005

(30) Foreign Application Priority Data

Mar. 12, 2001    (JP) .............................. 2001-368397

(51) Int. Cl.
*B01D 39/00*    (2006.01)
*B01D 71/06*    (2006.01)

(52) U.S. Cl. ...................... 210/504; 210/483; 210/488; 210/489; 210/490; 210/500.24; 210/500.37; 210/506

(58) Field of Classification Search ................ 210/483, 210/488, 489, 490, 500.24, 500.35, 500.37, 210/504, 506
See application file for complete search history.

(56) References Cited

U.S. PATENT DOCUMENTS

| | | | | |
|---|---|---|---|---|
| 4,936,998 A | * | 6/1990 | Nishimura et al. | 210/638 |
| 6,267,898 B1 | * | 7/2001 | Fukuda et al. | 210/767 |
| 6,352,642 B1 | * | 3/2002 | Fukuda et al. | 210/500.37 |

FOREIGN PATENT DOCUMENTS

| | | |
|---|---|---|
| JP | 2002-282351 | 10/2002 |
| JP | 2003-038641 | 2/2003 |

OTHER PUBLICATIONS

English Translation copy of JP 2003-038641.*
English Translation copy of JP 2002-282351.*

* cited by examiner

*Primary Examiner*—John Kim
(74) *Attorney, Agent, or Firm*—Young & Thompson

(57) ABSTRACT

It is intended to provide a filter for selectively removing leukocytes whereby leukocytes can be selectively and efficiently removed without worsening in the performance due to sterilization while causing little elution and minimizing loss in platelets. Namely, a filter for selectively removing leukocytes which is highly tolerant to sterilization and contains a polymer on the filter surface, characterized in that the polymer consists of a hydroxyalkyl (meth)acrylate unit having 3 or 4 carbon atoms in the alkyl moiety, a monomer unit having a basic nitrogen-containing functional group, and a monomer unit having an ethylene oxide chain with a repetition number of 2 to 9, the content of the monomer unit having the basic nitrogen-containing functional group ranges from 2% by mol to 9% by mol in the polymer, and the ethylene oxide chain content ranges from 1% by weight to 10% by weight in the polymer.

15 Claims, No Drawings

US 7,410,066 B2

FILTER FOR SELECTIVELY ELIMINATING LEUKOCYTES

TECHNICAL FIELD

The present invention relates to a filter for selectively removing leukocytes that can selectively remove leukocytes from blood and allow platelets to pass through.

BACKGROUND ART

Currently, component transfusion in which only blood components required for a patient are transfused is more popular in the field of transfusion. In component transfusion, leukocytes must be removed from various blood products to a level low enough to prevent side effects that may occur after transfusion. As a method for removing leukocytes, a filter method is widely accepted due to advantages such as excellent leukocyte removal capability, simple operation, and low cost.

In this case, a method of removing leukocytes using a filter after separating blood into each of its components and adjusting various blood component products requires a leukocyte removal operation for each blood component product. On the other hand, a method of adjusting each blood component product after removing only leukocytes from whole blood is very useful from the viewpoint of operability and cost, since only one leukocyte removal operation is necessary.

However, since currently commercially available filters for whole blood products also remove platelets, a platelet product cannot be prepared from a whole blood product obtained by filtration using these filters. Therefore, a high performance filter that can allow platelets and erythrocytes to pass through and selectively remove leukocytes is demanded.

There are several reports on filters to remove leukocytes from blood that can allow platelets and erythrocytes to pass through. Japanese Patent Publication No. 6-51060 discloses a filter containing a nonionic hydrophilic group and a basic nitrogen-containing functional group on the surface that can be prepared by coating with a copolymer containing hydroxyethyl methacrylate (hereinafter abbreviated as HEMA) and dimethylaminoethyl methacrylate. According to research conducted by the inventors of the present invention, the filter was found to have a problem of easily allowing polymers to be eluted in spite of its capability of allowing platelets to pass through due to the high hydrophilicity of the polymer. The present inventors have found that if hydroxypropyl methacrylate, which is a little more hydrophobic than HEMA, is used instead of the HEMA, the effect of preventing elution can be achieved. However, the filter encountered a new problem of decreasing the platelet recovery rate if the filter has been sterilized with high pressure steam.

The applicants of the present invention have disclosed, in Japanese Patent Application Laid-open No. 5-194243, a leukocyte-removing filter containing an ethylene oxide chain with 2-15 ethylene oxide repetitions and a basic nitrogen-containing functional group, in which the hydrophilicity is increased and the platelet recovery rate is improved by introducing the ethylene oxide chain onto the filter surface. However, the present inventors have found that elution of a polymer into blood may be anticipated, if the ethylene oxide chain is long or the content of the ethylene oxide chain is increased.

The applicants of the present invention have further disclosed a leukocyte-removing filter containing an ethylene oxide chain with two ethylene oxide repetitions in Japanese Patent Application Laid-open No. 2000-245833. However, this filter is also thought to have a risk of elution of a polymer into the blood due to the large content of ethylene oxide chain (14-38 wt %) in the polymer used in the examples.

Moreover, the applicants of the present invention have disclosed, in Japanese Patent Application Laid-open No.7-25776, a filter for selectively removing leukocytes with a polymer having both a hydrophobic moiety and an ethylene oxide chain with 2-100 ethylene oxide repetitions coated on the surface. The filter can remove leukocytes efficiently with little platelet adhesion, while inhibiting elution of polymers. However, the filter used in the examples may also have a risk of eluting the polymer into the blood due to the large content of ethylene oxide chain (59-74 wt %) in the polymer, although the polymer has hydrophobic moieties. In view of the fact that a polymer containing an ethylene oxide chain tends to be eluted at a low temperature rather than at a high temperature, the present inventors have investigated elution of a polymer containing methyl methacrylate (30 mol %) and methoxynonaethylene glycol methacrylate (70 mol %) with 9 ethylene oxide repetitions at a normal blood processing temperature (room temperature) and have found that 20% of the polymer was eluted. In addition, although high hydrophilicity is effective for suppressing platelet adhesion, a decrease in leukocyte capturing capability is anticipated. This problem did not surface in the patent specification due to the use of a concentrated platelet solution with a low leukocyte concentration in the examples. The present inventors have found that sufficient leukocyte removal capability cannot be obtained if whole blood with an overwhelmingly high leukocyte concentration as compared with a concentrated platelet solution is used.

There have been no filters for selective removal of leukocytes having excellent sterilization resistance, high safety due to the least elution of polymers into the blood, and high blood processing performance.

DISCLOSURE OF THE INVENTION

An object of the present invention is to provide a filter for selective removal of leukocytes, in which the problems in conventional leukocyte-removing filters such as deterioration of performance by sterilization treatment and easy elution of polymers at room temperature have been overcome, and which can selectively and efficiently remove leukocytes, while minimizing the loss of platelets even when processing human whole blood.

As a result of extensive studies to achieve the above object, the present inventors have found that, in a filter for selectively removing leukocytes containing a polymer on the surface of the filter, if a hydroxyalkyl (meth)acrylate unit with the alkyl group having 3 or 4 carbon atoms and a monomer unit having a basic nitrogen-containing functional group are used as the units forming the polymer for ensuring elution properties and blood processing performance, and if a small amount of a monomer unit containing an ethylene oxide chain with 2-9 ethylene oxide repetitions is added, a filter exhibiting extremely low elution properties, high leukocyte removal capability, a high platelet recovery rate, and superior sterilization resistance can be obtained. This finding has led to the completion of the present invention.

Specifically, the present invention relates to a filter for selectively removing leukocytes with excellent sterilization resistance containing a polymer on the surface, wherein the polymer is formed from a hydroxyalkyl (meth) acrylate unit with the alkyl moiety having 3 or 4 carbon atoms, a monomer unit having a basic nitrogen-containing functional group, and a monomer unit containing an ethylene oxide chain with 2-9 ethylene oxide repetitions, with the content of the monomer unit having a basic nitrogen-containing functional group being 2-9 mol % and the content of the ethylene oxide chain being 1-10 wt %.

In a conventional polymer introduced onto the surface of the filter base material, a hydroxymethyl (meth)acrylate unit or hydroxyethyl (meth)acrylate unit with 1 or 2 carbon atoms has been used as the alkyl moiety of the hydroxyalkyl (meth) acrylate unit. In the present invention, hydroxypropyl (meth) acrylate or hydroxybutyl (meth)acrylate with 3 or 4 carbon atoms has been selected to overcome the elution problem while maintaining adequate hydrophilicity.

In addition, the leukocyte removal capability was stabilized at a higher level and the platelet recovery rate was improved by selecting the amount of the monomer unit having a basic nitrogen-containing functional group in the polymer in the range of 2-9 mol %.

Furthermore, elution of the polymer into the blood was suppressed and a decrease in the platelet recovery rate was reduced by selecting the number of ethylene oxide repetitions in the ethylene oxide chain forming the polymer in the range of 2-9 and selecting the amount of the ethylene oxide chain in the range of 1-10 wt %. Moreover, the decrease in the platelet recovery rate due to sterilization at a high temperature was unexpectedly inhibited by incorporating the ethylene oxide chain.

In the present invention, the polymer is preferably a vinyl-type polymer. The weight average molecular weight of the polymer is 100,000-500,000. It is preferable that the content of the polymer having a weight average molecular weight of 10,000 or less be less than 10 wt %. It is further preferable that the ratio of the content of the ethylene oxide chain in the polymer to the weight average molecular weight of the polymer be from $3.5 \times 10^{-6}$ to $40 \times 10^{-6}$.

In addition, to selectively remove leukocytes from human whole blood, the amount of the polymer introduced per unit surface area of the filter base material is preferably 90-300 mg/m$^2$.

BEST MODE FOR CARRYING OUT THE INVENTION

The present invention will now be explained in detail.

The polymer in the present invention refers to a polymer formed from a hydroxyalkyl (meth) acrylate unit with the alkyl moiety having 3 or 4 carbon atoms, a monomer unit having a basic nitrogen-containing functional group, and a monomer unit having an ethylene oxide chain. The (meth) acrylate in the present invention includes acrylate and methacrylate.

The polymer can be obtained by a known polymerization method. For example, chain reactions such as addition polymerization, cyclization polymerization, isomerization polymerization, and ring-opening polymerization and consecutive reactions such as elimination reaction, poly addition, polycondensation, and addition polycondensation can be given. Of these, from the viewpoint of easy availability, handling ease, easy synthesis, and the like of a monomer, a polymer obtained by addition polymerization (vinyl polymerization) of a monomer having a vinyl group for a polymerizable part is preferable. Either a random copolymer or a block copolymer can be used. The term "unit" in the present invention is a part of a polymer and refers to a minimum repeating unit formed by polymerization or the like of a monomer.

The hydroxyalkyl (meth) acrylate having 3 or 4 carbon atoms in the alkyl moiety used in the present invention is effective for increasing the platelet recovery rate and, at the same time, suppressing elution of the polymer due to the possession of a hydrophilic hydroxyl group and a hydrophobic alkyl chain. Moreover, moderately high wettability with blood increases the effective utilization ratio on the surface of the filter and is effective also in the increase in the leukocyte removal capability. An additional advantage is little elution after sterilization with γ-rays or electron beams. If the carbon atoms in the alkyl moiety are 2 or less, the polymer may be eluted due to high hydrophilicity; if 5 or more, the platelet recovery rate may decrease due to high hydrophobicity. Specifically, the hydroxyalkyl (meth)acrylate includes hydroxypropyl (meth)acrylate, hydroxybutyl (meth)acrylate, their isomers, and mixtures of the isomers. Of these, methacrylic acid derivatives are preferable in view of ease of handling and the like, with the most preferable compound being hydroxypropyl methacrylate.

Materials having a basic nitrogen-containing functional group generally have characteristics of producing positive charges on the surface in a cell suspension represented by blood and causing leukocytes having negative charges to adhere. The basic nitrogen-containing functional group must be included in the polymer to provide more stable and high leukocyte removal capability. The amount of the monomer unit having a basic nitrogen-containing functional group in the polymer is in the range of 2-9 mol %, and preferably 3-7 mol %. If less than 2 mol %, it is difficult to obtain sufficient leukocyte removal capability; if more than 9 mol %, platelets are easily caused to adhere and it is difficult to achieve a high platelet recovery rate.

A primary amino group, secondary amino group, tertiary amino group, quaternary ammonium group, pyridyl group, imidazoyl group, and the like can be given as the basic nitrogen-containing functional groups. The monomers having such a basic nitrogen-containing functional group include, but are not limited to, vinyl derivatives of a nitrogen-containing aromatic compound such as vinylamine, 2-vinylpyridine, 4-vinylpyridine, 2-methyl-5-vinylpyridine, 4-vinylimidazole, N-vinyl-2-ethylimidazole, N-vinyl-2-methylimidazole; dimethylaminoethyl. (meth)acrylate, diethylaminoethyl (meth)acrylate, 3-dimethylamino-2-hydroxypropyl (meth) acrylate, dimethylaminoethyl (meth)acrylamide, diethylaminoethyl (meth)acrylamide, p-dimethylaminomethylstyrene, p-diethylaminoethylstyrene; and quaternary ammonium salts prepared by reacting the compounds with an alkyl halide. From the viewpoint of ease of availability and handling, acrylic acid derivatives and methacrylic acid derivatives are preferable, with dimethylaminoethyl (meth)acrylate and diethylaminoethyl (meth)acrylate containing a tertiary amino group being particularly preferable.

The monomer unit having an ethylene oxide chain in the polymer exhibits a high platelet adhesion controlling effect due to outstanding conformity to blood possessed by the ethylene oxide chain. In addition, incorporation of a small amount of ethylene oxide chain into the polymer provides the polymer with an effect of inhibiting an increase in platelet adhesiveness due to autoclave sterilization, that is, sterilization resistance as a novel function. The monomer having an ethylene oxide chain used in the present invention contains 2-9 repetitions in the ethylene oxide chain. If the number of repetitions is less than 2, it is difficult to obtain a sufficient platelet adhesion controlling effect. Moreover, it tends to become difficult to control the decrease in the platelet recovery rate due to autoclave sterilization. If the number of repetitions is more than 9, the polymer becomes less adhesive to the filter base material, increasing a tendency of eluting itself (polymer) more easily when blood comes into contact with the filter base material. The number of repetitions of 2-4 is more preferable from the viewpoint of easy availability, handling ease, easy synthesis, and the like. The number of repetitions of 2 is most preferable. Specific examples include, but are not limited to, methoxydiethylene glycol (meth)acrylate, methoxytriethylene glycol (meth)acrylate, and methoxytetraethylene glycol (meth)acrylate. The monomers are preferably nonprotonic for ensuring elution properties.

The content of ethylene oxide chain in the polymer in the present invention refers to the weight percent (wt %) of the ethylene oxide chain in the weight of polymer. The content of ethylene oxide chain in the polymer is 1-10 wt %, and preferably 3-8 wt %. This is because an ethylene oxide chain content in this range can ensure excellent autoclave sterilization resistance while controlling elution. If less than 1 wt %, the platelet recovery rate after autoclave sterilization decreases; if more than 10 wt %, elution to the blood increases.

The contents of the basic nitrogen-containing functional group and the ethylene oxide chain can be determined by known methods such as attenuated total reflection infrared (ATR-IR) spectroscopy using a multiple total reflection infrared spectrometer, nuclear magnetic resonance (NMR) spectroscopy, and elemental analysis.

The amount of polymer introduced per unit surface area of the filter base material is 90-300 mg/m$^2$, and preferably 120-250 mg/m$^2$. If less than 90 mg/m$^2$, the surface of the filter may not be completely covered with the polymer and the function of the polymer may not be efficiently exhibited. When human whole blood is used, a sufficient platelet recovery rate may not be obtained. If more than 300 mg/m$^2$, the specific surface area of the filter is too small to provide sufficient leukocyte removal capability.

The amount of polymer introduced per unit surface area of the filter base material herein refers to the weight of polymer introduced for 1 m$^2$ of the filter base material. The surface area of the filter base material can be determined from the specific surface area measured by the BET adsorption method using krypton gas as the adsorption gas at an adsorption temperature equivalent to liquid nitrogen temperature.

The amount of polymer introduced onto the surface of the filter base material in the present invention can be calculated simply from the weight change before and after introducing the polymer. When there is a good solvent which dissolves only the polymer, it is possible to determine the amount of polymer from the weight change of the filter before and after dissolving the polymer in the good solvent, even if the weight before introducing the polymer is unknown. A method of dissolving the whole filter in a solvent and calculating the amount of polymer by the NMR method can also be used. If the polymer contains a chargeable functional group such as an amino group and the copolymerization composition is known, a coloring matter adsorption method using a coloring matter which is ionically adsorbed on the chargeable functional group can be used.

As a method for confirming the presence of polymer on the surface of the filter for selectively removing leukocytes, known analytical methods such as X-ray photoelectron spectroscopy (XPS) and secondary ion mass spectroscopy (SIMS) can be used.

As a method for introducing the polymer onto the surface of the filter base material, a common surface modification method such as a method of coating the surface of the filter base material with a polymer can be used. As a pre-treatment for polymer introduction to increase adhesion of the polymer of the present invention to the filter base material, the surface of the filter base material may be treated with a suitable agent such as an acid or alkali or may be irradiated with plasma or electron beams. Adhesion of the polymer to the filter base material may be further increased by post-treatment such as a heat treatment or irradiation with γ-rays, electron beams, or the like after introducing the polymer onto the surface.

The weight average molecular weight of the polymer used in the present invention is preferably 100,000-500,000. If the weight average molecular weight is less than 100,000, the polymer may be easily eluted into the blood when coming into contact with the blood. If the weight average molecular weight is more than 500,000, not only is a coating operation difficult, but also the blood flow is retarded when the polymer comes into contact with the blood. In either case, the filter may not exhibit sufficient performance as a filter for selectively removing leukocytes. If the weight average molecular weight exceeds 500,000, the platelet recovery rate after autoclave sterilization may decrease. For ensuring elution properties, the content of the polymer with a weight average molecular weight of 10,000 or less is preferably less than 10 wt %.

Although the molecular weight can be determined by various known methods, a value determined by gel permeation chromatography (hereinafter abbreviated to GPC) using polymethyl methacrylate as a standard was used in the present invention. Specifically, the weight average molecular weight and the content of the polymer with a weight average molecular weight of 10,000 or less were determined using STANDARD M-75 (manufactured by Showa Denko Co., Ltd.) as a standard polymethyl methacrylate sample, TSK gel α-M (manufactured by Tosoh Corp.) as a GPC column, dimethylformamide (containing 10 mmol/l of lithium bromide) as an eluant, and a refractive index detector for detection under the conditions of a flow rate of 1.0 ml/min and a temperature of 40° C.

In the present invention, the ratio of the ethylene oxide chain content in the polymer to the weight average molecular weight of the polymer (hereinafter abbreviated to EO/Mw) is preferably from $3.5 \times 10^{-6}$ to $40 \times 10^{-6}$. As mentioned above, the ratio of the ethylene oxide chain content in the polymer to the weight average molecular weight of the polymer is closely related to the elution properties and sterilization resistance of the polymer. Specifically, if the EO/Mw is less than $3.5 \times 10^{-6}$, there is a tendency of too small a content of the ethylene oxide chain or too great a weight average molecular weight, giving rise to a decrease in the platelet recovery rate after autoclave sterilization. If the EO/Mw is more than $40 \times 10^{-6}$, there is a tendency of too great a content of the ethylene oxide chain or too small a weight average molecular weight, giving rise to an increased elution of the polymer into the blood. The EO/Mw in the present invention is a value obtained by dividing the ethylene oxide chain content (wt %) by the weight average molecular weight of the polymer.

The average pore diameter of the filter of the present invention is 1-30 μm, preferably 1-20 μm, and more preferably 2-10 μm. If the average pore diameter is less than 1 μm, the pressure loss when filtering whole blood and the like may be too great to use the filter in practice; if more than 30 μm, on the other hand, leukocytes may not be sufficiently removed because leukocytes have a reduced chance of contact with the filter. The average pore diameter used herein refers to an average pore diameter of a square (5 cm×5 cm) filter with a thickness of about 0.6 mm measured by a method conforming to the bubble pointing method in ASTM F316-86 using an automatic pore measurement apparatus (manufactured by Porous Materials Inc.) after the sample has been immersed in a fluorine-containing inert liquid FC-43 (manufactured by Sumitomo 3M, Ltd.).

The bulk density of the filter of the present invention is 0.10-0.50 g/cm$^3$, preferably 0.10-0.35 g/cm$^3$, and more preferably 0.15-0.30 g/cm$^3$. If the bulk density is less than 0.10 g/cm$^3$, the mechanical strength of the filter is insufficient and the filter may be deformed during blood filtration. If the bulk density is more than 0.50 g/cm$^3$, the blood permeation resistance is increased, giving rise to deficiencies such as extension of filtration time. The bulk density herein refers to a value obtained by dividing the weight of the filter by the product of the thickness and the area which are determined from the size of the filter, wherein the thickness is an average of measured values found at arbitrarily selected three or more points.

A base material of any form can be used for the filter for leukocyte removal of the present invention without any specific limitations, inasmuch as such a base material has pores allowing blood to permeate through and causes minimum damage to the blood cells. Specific materials include fibrous media such as natural fiber, glass fiber, knit, fabric, and nonwoven fabric, porous membranes, and sponge-like structural materials having a three-dimensional network of continuous pores.

Organic polymer materials are preferable materials for forming the filter base material of the present invention due to their excellent processability such as cutting. Specific examples include, but are not limited to, polyolefin such as polyethylene and polypropylene, polyester, polyurethane, polyamide, ethylene-vinyl alcohol copolymer, polyacrylate, polymethacrylate, polysulfone, cellulose, cellulose acetate, polyvinyl fluoride, polyvinylidene fluoride, polyethersulfone, butadiene-acrylonitrile copolymer, polyethylene terephthalate, polybuthylene terephthalate, polytetraethylene terephthalate, and a mixture of these polymers.

Whole blood in the present invention refers to a whole blood product containing an anticoagulant such as ACD (acid·citrate·dextrose) or CPD (citrate·phosphate·dextrose) that has been stored for not more than three days, preferably not more than one day, and more preferably not more than eight hours after collection. The storage temperature of the whole blood after collection until the time when the blood is filtered is preferably from 4° C. to 30° C. More preferably, the whole blood product is preserved at a temperature from 15° C. to 25° C. A whole blood product preserved for a period longer than three days or preserved at a temperature of less than 4° C. is not preferable because functions of platelets in such a whole blood product may have been impaired. A whole blood product preserved at a temperature above 30° C. is not preferable, since plasma proteins may be denatured during preservation and an increase in the platelet recovery rate may not be expected.

EXAMPLES

The present invention is described below by examples, which should not be construed as limiting the present invention.

Example 1

Synthesis of Polymer

One example of the method of synthesizing the polymer used for coating the surface of a filter base material will be given. A reaction vessel equipped with a reflux condenser was charged with ethanol (230 g). After bubbling nitrogen into ethanol and stirring the mixture at 70° C. for one hour, monomers were added dropwise over 120 minutes while maintaining a nitrogen atmosphere. An initiator solution was added dropwise at the same time over 420 minutes. After completing the addition of the initiator solution, the monomers were polymerized for further two hours. As the monomers, a liquid mixture of 116.04 g (0.81 mol) of hydroxypropyl methacrylate (hereinafter abbreviated to HPMA), 4.04 g (26 mmol) of dimethylaminoethyl methacrylate which is a monomer having a basic nitrogen-containing functional group (hereinafter abbreviated to DM), and 4.83 g (26 mmol) of methoxydiethylene glycol methacrylate which is a monomer having an ethylene oxide chain with 2 ethylene oxide repetitions (hereinafter abbreviated to DEG) was used. The molar ratio of the monomers was 94.0 mol % (HPMA) 3.0 mol % (DM) 3.0 mol % (DEG). A solution of 0.70 g of 2,2'-azobis(2,4-dimethylvaleronitrile) (V-65) in ethanol was used as the initiator solution. The polymer solution was added dropwise to purified water to cause the polymer to precipitate. The collected polymer precipitate was cut into pieces and again put into purified water, followed by stirring for one hour to wash the polymer. Next, the washed polymer was dried under vacuum at 40° C. to obtain the target polymer (hereinafter DPM943). The composition of the resulting polymer was analyzed from the integral value of NMR measurement, confirming that the composition was almost in agreement with the charged monomer composition. Accordingly, the content of DM unit was 3 mol % and the ethylene oxide chain content measured by the NMR method was 1.8 wt %. The weight average molecular weight determined by GPC was $3.1 \times 10^5$ and the content of the polymer having a weight average molecular weight of 10,000 or less was 2 wt %. The ethylene oxide chain content in the polymer in Examples and Comparative Examples of the present invention was determined from integrated values of signals found by $^1$H-NMR measurement of a DMF (dimethylformamide) solution of the polymer at a concentration of 5 wt/vol %, using JNM-LA400 (manufactured by JEOL Ltd.) at a frequency of 400 MHz at room temperature.

(Preparation of filter material)

Next, an example of the method for preparing the filter material is shown. 10 g of the polymer (DPM943) obtained above was dissolved in 100 g of a mixed solvent of isopropanol and purified water. A nonwoven fabric made from polyethylene terephthalate (average pore diameter: 7 μm, a weight per unit area: 40 g/m$^2$) was dipped in the solution. After removing excessive liquid, the nonwoven fabric was dried at room temperature for 16 hours to obtain the target filter material. The bulk density of the filter material was 0.24 g/cm$^3$.

Next, the surface area of the filter base material was measured. The BET adsorption method was used as the measuring method using Accusorb 2100E (manufactured by Shimadzu Corp.) as a measuring instrument and krypton gas as adsorption gas at an adsorption temperature equivalent to liquid nitrogen temperature. As a result of measurement, the specific surface area of the filter base material was 1.47 m$^2$/g and the polymer weight per unit surface area of the filter base material was 210 mg/m$^2$.

In Examples and Comparative Examples of the present invention, the amount of the introduced polymer was determined as follows. After measuring the weight of the filter material, Wf (g), the filter material was put into ethanol and shaken to completely dissolve the polymer. The filter material was recovered and dried to measure the weight Wb (g). The amount of the polymer introduced per unit surface area of the filter base material, Wp (mg/m$^2$), was calculated by the following formula.

$$Wp = (Wf - Wb) \times 1000 / Wb / S$$

wherein S is the specific surface area of the filter base material (m²/g).

(Elution Test)

The method of the elution test was as follows. The filter with a size of 5 cm×5 cm thus prepared was immersed in purified water for 16 hours at 25° C. After drying under vacuum, the weight was measured to determine the weight change of the polymer before and after immersion according to the following formula (1).

Weight change (%) =(1−[weight of polymer in filter (after immersion)]/[weight of polymer in filter (before immersion)]×100      (1)

As a result of the elution test, the weight change was found to be 0.2%. The weight of polymers was determined by completely dissolving each polymer in a good solvent and calculating the weight difference before and after dissolution. Absence of polymers in the filter material after dissolution was confirmed by NMR analysis.

(Evaluation of Blood)

Next, a test method for evaluating the leukocyte removal capability and platelet recovery rate will be described. Whole blood prepared by adding 14 ml of a filtered CPD solution (a solution prepared by dissolving 2.630 g of trisodium citrate dihydrate, 0.327 g of citric acid monohydrate, 0.251 g of sodium dihydrogen phosphate dihydrate, and 2.320 g of glucose in 100 ml of distilled water for injection, followed by filtration using a 0.2 μm filter) to 100 ml of blood immediately after collection, mixing the mixture, and allowing to stand for two hours was used for the blood evaluation. This whole blood is hereinafter referred to as "blood before filtration."

16 sheets of the filter were packed in a column with an effective filtration area of 1.3 cm² and the whole blood was caused to pass through the column at a flow rate of 0.9 ml/min to collect 8 ml of blood (hereinafter referred to as "blood after filtration." The leukocyte removal capability was calculated according to the following formula (2) using the flow cytometory method (apparatus: FACS Calibur manufactured by Becton, Dickinson and Company).

Leukocyte removal capability=−log ([number of leukocytes (in blood after filtration)]/[number of leukocytes (in blood before filtration)])      (2)

Each sample was prepared by collecting 100 μl of blood and using a leucocount kit containing beads (Nippon Becton Dickinson Company, Ltd.). The platelet recovery rate was determined by applying the result of measurement using an automatic blood cell counter (Sysmex K4500 manufactured by Toa Medical Co., Ltd.) to the following formula (3).

Platelet recovery rate=([platelet concentration (in blood after filtration)]/[platelet concentration (in blood before filtration)])×100      (3)

As a result, the leukocyte removal capability was 3.6 and the platelet recovery rate was 84%.

The same elution test and blood evaluation were carried out using the filter after autoclave sterilization (118° C., 30 minutes). As a result, the weight change was 0.2%, the leukocyte removal capability was 3.8, and the platelet recovery rate was 81%. The results of elution test and blood evaluation in the following Examples are shown in Table 1 together with the results of Example 1.

Example 2

A polymer was synthesized in the same manner as in Example 1, except for using 90.0 mol % of HPMA, 3.0 mol % of DM, and 7.0 mol % of DEG. The DM unit content and the ethylene oxide chain content in the polymer (hereinafter referred to as DPM903) thus obtained were respectively 3 mol % and 4.2 wt %. The weight average molecular weight determined by GPC was $2.9 \times 10^5$ and the content of the polymer having a weight average molecular weight of 10,000 or less was 2 wt %. A filter material was prepared, and the elution test and blood evaluation were carried out in the same manner as in Example 1 to find that, in the filter material before sterilization treatment, the weight of polymer per unit surface area was 202 mg/m², the weight change was 1.0%, the leukocyte removal capability was 3.7, and the platelet recovery rate was 86%. In the filter material after autoclave sterilization, the weight change was 0.8%, the leukocyte removal capability was 4.0, and the platelet recovery rate was 84%.

The same elution test and blood evaluation were carried out using a filter obtained by treating an untreated filter with γ-rays sterilization (25 kGy). As a result, the weight change was 1.0%, the leukocyte removal capability was 3.8, and the platelet recovery rate was 86%.

0.5 g of DPM903 was dissolved in 100 g of a mixed solvent of isopropanol and purified water. The solution was applied to a polyethylene terephthalate film and, after removing excessive liquid, dried at room temperature for 16 hours to obtain a film coated with DPM903. The film was sterilized with high pressure steam under the same conditions as in Example 1 to inspect the surface condition using a scanning electron microscope (magnification 3,000). A scanning electron microscope photograph confirmed a very smooth surface of the film.

Example 3

A polymer was synthesized in the same manner as in Example 1, except for using 86.0 mol % of HPMA, 3.0 mol % of DM, and 11.0 mol % of DEG. The DM unit content and the ethylene oxide chain content in the polymer (hereinafter referred to as DPM863) thus obtained were respectively 3 mol % and 6.5 wt %. The weight average molecular weight determined by GPC was $3.2 \times 10^5$ and the content of the polymer having a weight average molecular weight of 10,000 or less was 2 wt %.

A filter material was prepared, and the elution test and blood evaluation were carried out in the same manner as in Example 1 to find that, in the filter material before sterilization treatment, the weight of polymer per unit surface area was 197 mg/m², the weight change was 1.5%, the leukocyte removal capability was 3.8, and the platelet recovery rate was 87%. In the filter material after autoclave sterilization, the weight change was 1.4%, the leukocyte removal capability was 3.9, and the platelet recovery rate was 86%.

Example 4

A polymer was synthesized in the same manner as in Example 1, except for using 82.0 mol % of HPMA, 3.0 mol % of DM, and 15.0 mol % of DEG. The DM unit content and the ethylene oxide chain content in the polymer (hereinafter referred to as DPM823) thus obtained were respectively 3 mol % and 8.7 wt %. The weight average molecular weight determined by GPC was $3.3 \times 10^5$ and the content of the polymer having a weight average molecular weight of 10,000 or less was 2 wt %.

A filter material was prepared, and the elution test and blood evaluation were carried out in the same manner as in Example 1 to find that, in the filter material before sterilization treatment, the weight of polymer per unit surface area was 204 mg/M², the weight change was 2.9%, the leukocyte removal capability was 3.5, and the platelet recovery rate was 88%. In the filter material after autoclave sterilization, the weight change was 2.6%, the leukocyte removal capability was 3.7, and the platelet recovery rate was 88%.

Example 5

A polymer was synthesized in the same manner as in Example 1, except for using 88.0 mol % of HPMA, 5.0 mol % of DM, and 7.0 mol % of DEG. The DM unit content and the ethylene oxide chain content in the polymer (hereinafter referred to as DPM885) thus obtained were respectively 5 mol % and 4.2 wt %. The weight average molecular weight determined by GPC was $3.0 \times 10^5$ and the content of the polymer having a weight average molecular weight of 10,000 or less was 2 wt %.

A filter material was prepared, and the elution test and blood evaluation were carried out in the same manner as in Example 1 to find that, in the filter material before sterilization treatment, the weight of polymer per unit surface area was 199 mg/m$^2$, the weight change was 2.5%, the leukocyte removal capability was 3.8, and the platelet recovery rate was 85%. In the filter material after autoclave sterilization, the weight change was 2.3%, the leukocyte removal capability was 4.0, and the platelet recovery rate was 83%.

Example 6

A polymer was synthesized in the same manner as in Example 1, except for using 86.0 mol % of HPMA, 7.0 mol % of DM, and 7.0 mol % of DEG. The DM unit content and the ethylene oxide chain content in the polymer (hereinafter referred to as DPM867) thus obtained were respectively 7 mol % and 4.2 wt %. The weight average molecular weight determined by GPC was $2.9 \times 10^5$ and the content of the polymer having a weight average molecular weight of 10,000 or less was 2 wt %.

A filter material was prepared, and the elution test and blood evaluation were carried out in the same manner as in Example 1 to find that, in the filter material before sterilization treatment, the weight of polymer per unit surface area was 205 mg/m$^2$, the weight change was 2.8%, the leukocyte removal capability was 3.9, and the platelet recovery rate was 84%. In the filter material after autoclave sterilization, the weight change was 2.5%, the leukocyte removal capability was 4.0, and the platelet recovery rate was 83%.

Example 7

A polymer was synthesized in the same manner as in Example 1, except for using 94.0 mol % of HPMA, 3.0 mol % of DM, and 3.0 mol % of methoxytetraethylene glycol methacrylate with four ethylene oxide repetitions in the ethylene oxide chain (hereinafter referred to as TEG). The DM unit content and the ethylene oxide chain content in the polymer (hereinafter referred to as TPM943) thus obtained were respectively 3 mol % and 3.6 wt %. The weight average molecular weight determined by GPC was $3.2 \times 10^5$ and the content of the polymer having a weight average molecular weight of 10,000 or less was 2 wt %.

A filter material was prepared, and the elution test and blood evaluation were carried out in the same manner as in Example 1 to find that, in the filter material before sterilization treatment, the weight of polymer per unit surface area was 206 mg/m$^2$, the weight change was 1.5%, the leukocyte removal capability was 3.5, and the platelet recovery rate was 87%. In the filter material after autoclave sterilization, the weight change was 1.3%, the leukocyte removal capability was 3.7, and the platelet recovery rate was 85%.

Example 8

A polymer was synthesized in the same manner as in Example 1, except for using 95.0 mol % of HPMA, 3.0 mol % of DM, and 2.0 mol % of methoxynonaethylene glycol methacrylate with nine ethylene oxide repetitions in the ethylene oxide chain (hereinafter referred to as NEG). The DM unit content and the ethylene oxide chain content in the polymer (hereinafter referred to as NPM953) thus obtained were respectively 3 mol % and 5.2 wt %. The weight average molecular weight determined by GPC was $3.4 \times 10^5$ and the content of the polymer having a weight average molecular weight of 10,000 or less was 2 wt %.

A filter material was prepared, and the elution test and blood evaluation were carried out in the same manner as in Example 1 to find that, in the filter material before sterilization treatment, the weight of polymer per unit surface area was 208 mg/m$^2$, the weight change was 2.3%, the leukocyte removal capability was 3.5, and the platelet recovery rate was 88%. In the filter material after autoclave sterilization, the weight change was 2.1%, the leukocyte removal capability was 3.6, and the platelet recovery rate was 87%.

Example 9

A polymer was synthesized in the same manner as in Example 1, except for using 87.0 mol % of hydroxybutyl methacrylate (hereinafter referred to as HBMA), 3.0 mol % of DM, and 10.0 mol % of DEG. The DM unit content and the ethylene oxide chain content in the polymer (hereinafter referred to as DBM873) thus obtained were respectively 3 mol % and 5.5 wt %. The weight average molecular weight determined by GPC was $3.0 \times 10^5$ and the content of the polymer having a weight average molecular weight of 10,000 or less was 2 wt %.

A filter material was prepared, and the elution test and blood evaluation were carried out in the same manner as in Example 1 to find that, in the filter material before sterilization treatment, the weight of polymer per unit surface area was 202 mg/m$^2$, the weight change was 0.7%, the leukocyte removal capability was 3.7, and the platelet recovery rate was 83%. In the filter material after autoclave sterilization, the weight change was 0.7%, the leukocyte removal capability was 3.9, and the platelet recovery rate was 80%.

Example 10

A polymer was synthesized in the same manner as in Example 1, except for using 80.0 mol % of HPMA, 5.0 mol % of DM, 15.0 mol % of DEG, 330 g of ethanol, and 0.78 g of V-65. The DM unit content and the ethylene oxide chain content in the polymer (hereinafter referred to as DPM805L) thus obtained were respectively 5 mol % and 8.7 wt %. The weight average molecular weight determined by GPC was $1.3 \times 10^5$ and the content of the polymer having a weight average molecular weight of 10,000 or less was 4 wt %.

A filter material was prepared, and the elution test and blood evaluation were carried out in the same manner as in Example 1 to find that, in the filter material before sterilization treatment, the weight of polymer per unit surface area was 202 mg/m$^2$, the weight change was 4.7%, the leukocyte removal capability was 3.8, and the platelet recovery rate was 85%. In the filter material afterautoclave sterilization, the weight change was 4.3%, the leukocyte removal capability was 3.8, and the platelet recovery rate was 84%.

Example 11

A polymer was synthesized in the same manner as in Example 1, except for using 80.0 mol % of HPMA, 5.0 mol % of DM, 15.0 mol % of DEG, a monomer dropping time of 90 minutes, and 0.50 g of V-65. The DM unit content and the ethylene oxide chain content in the polymer (hereinafter referred to as DPM805H) thus obtained were respectively 5 mol % and 8.7 wt %. The weight average molecular weight determined by GPC was $4.4 \times 10^5$ and the content of the polymer having a weight average molecular weight of 10,000 or less was 2 wt %.

A filter material was prepared, and the elution test and blood evaluation were carried out in the same manner as in Example 1 to find that, in the filter material before sterilization treatment, the weight of polymer per unit surface area was 205 mg/m$^2$, the weight change was 2.0%, the leukocyte removal capability was 3.9, and the platelet recovery rate was 84%. In the filter material after autoclave sterilization, the weight change was 1.7%, the leukocyte removal capability was 4.0, and the platelet recovery rate was 82%.

Example 12

A polymer was synthesized in the same manner as in Example 1, except for using 82.0 mol % of HPMA, 3.0 mol % of DM, 15.0 mol % of DEG, a monomer dropping time of 90 minutes, and 0.40 g of V-65. The DM unit content and the ethylene oxide chain content in the polymer (hereinafter referred to as DPM823H) thus obtained were respectively 3 mol % and 8.7 wt %. The weight average molecular weight determined by GPC was $5.5 \times 10^5$ and the content of the polymer having a weight average molecular weight of 10,000 or less was 2 wt %.

A filter material was prepared, and the elution test and blood evaluation were carried out in the same manner as in Example 1 to find that, in the filter material before sterilization treatment, the weight of polymer per unit surface area was 210 mg/m$^2$, the weight change was 1.8%, the leukocyte removal capability was 3.6, and the platelet recovery rate was 87%. In the filter material after autoclave sterilization, the weight change was 1.5%, the leukocyte removal capability was 3.7, and the platelet recovery rate was 82%.

Example 13

A polymer was synthesized in the same manner as in Example 1, except for using 88.0 mol % of HPMA, 5.0 mol % of DM, 7.0 mol % of DEG, 330 g of ethanol, and 0.78 g of V-65. The DM unit content and the ethylene oxide chain content in the polymer (hereinafter referred to as DPM885L) thus obtained were respectively 5 mol % and 4.2 wt %. The weight average molecular weight determined by GPC was $1.4 \times 10^5$ and the content of the polymer having a weight average molecular weight of 10,000 or less was 4 wt %.

A filter material was prepared, and the elution test and blood evaluation were carried out in the same manner as in Example 1 to find that, in the filter material before sterilization treatment, the weight of polymer per unit surface area was 199 mg/m$^2$, the weight change was 2.8%, the leukocyte removal capability was 3.7, and the platelet recovery rate was 88%. In the filter material after autoclave sterilization, the weight change was 2.6%, the leukocyte removal capability was 3.9, and the platelet recovery rate was 88%.

Example 14

A polymer was synthesized in the same manner as in Example 1, except for using 94.0 mol % of HPMA, 3.0 mol % of DM, 3.0 mol % of DEG, 330 g of ethanol, a polymerization temperature of 87° C., and 0.84 g of V-65. The DM unit content and the ethylene oxide chain content in the polymer (hereinafter referred to as DPM943L) thus obtained were respectively 3 mol % and 1.8 wt %. The weight average molecular weight determined by GPC was $0.8 \times 10^5$ and the content of the polymer having a weight average molecular weight of 10,000 or less was 5 wt %.

A filter material was prepared, and the elution test and blood evaluation were carried out in the same manner as in Example 1 to find that, in the filter material before sterilization treatment, the weight of polymer per unit surface area was 209 mg/m$^2$, the weight change was 4.5%, the leukocyte removal capability was 3.6, and the platelet recovery rate was 84%. In the filter material after autoclave sterilization, the weight change was 4.2%, the leukocyte removal capability was 3.7, and the platelet recovery rate was 83%.

Example 15

A polymer was synthesized in the same manner as in Example 1, except for using 93.0 mol % of HPMA, 5.0 mol % of DM, and 2.0 mol % of DEG, a monomer dropping time of 90 minutes, and 0.50 g of V-65. The DM unit content and the ethylene oxide chain content in the polymer (hereinafter referred to as DPM935) thus obtained were respectively 5 mol % and 1.2 wt %. The weight average molecular weight determined by GPC was $4.5 \times 10^5$ and the content of the polymer having a weight average molecular weight of 10,000 or less was 2 wt %.

A filter material was prepared, and the elution test and blood evaluation were carried out in the same manner as in Example 1 to find that, in the filter material before sterilization treatment, the weight of polymer per unit surface area was 212 mg/m$^2$, the weight change was 0.1%, the leukocyte removal capability was 3.7, and the platelet recovery rate was 84%. In the filter material after autoclave sterilization, the weight change was 0.1%, the leukocyte removal capability was 3.8, and the platelet recovery rate was 80%.

Comparative Example 1

A polymer was synthesized in the same manner as in Example 1, except for using 97.0 mol % of HPMA and 3.0 mol % of DM. The DM unit content and the ethylene oxide chain content in the polymer (hereinafter referred to as DPM973) thus obtained were respectively 3 mol % and 0 wt %. The weight average molecular weight determined by GPC was $2.8 \times 10^5$ and the content of the polymer having a weight average molecular weight of 10,000 or less was 2 wt %.

A filter material was prepared, and the elution test and blood evaluation were carried out in the same manner as in Example 1 to find that, in the filter material before sterilization treatment, the weight of polymer per unit surface area was 198 mg/m$^2$, the weight change was 0.1%, the leukocyte removal capability was 3.5, and the platelet recovery rate was 80%. In the filter after autoclave sterilization, the weight change was 0.1%, the leukocyte removal capability was 3.8, and the platelet recovery rate was 65%.

0.5 g of DPM973 was dissolved in 100 g of a mixed solvent of isopropanol and purified water. The solution was applied to a polyethylene terephthalate film and, after removing excessive liquid, dried at room temperature for 16 hours to obtain a film coated with DPM973.

The film was sterilized with high pressure steam under the same conditions as in Example 1 to inspect the surface condition using a scanning electron microscope (magnification 3,000). The electron microscope photograph showed irregularities on the film surface due to detachment of the polymer from the film.

Comparative Example 2

A polymer was synthesized in the same manner as in Example 1, except for using 75.0 mol % of HPMA, 3.0 mol % of DM, and 22.0 mol % of DEG. The DM unit content and the ethylene oxide chain content in the polymer (hereinafter referred to as DPM753) thus obtained were respectively 3 mol % and 12.6 wt %. The weight average molecular weight determined by GPC was $3.0 \times 10^5$ and the content of the polymer having a weight average molecular weight of 10,000 or less was 2 wt %.

A filter was prepared, and the elution test and blood evaluation were carried out in the same manner as in Example 1 to find that, in the filter material before sterilization treatment, the weight of polymer per unit surface area was 199 mg/m$^2$, the weight change was 11.4%, the leukocyte removal capability was 3.3, and the platelet recovery rate was 82%. In the filter material after autoclave sterilization, the weight change was 10.9%, the leukocyte removal capability was 3.4, and the platelet recovery rate was 82%.

Comparative Example 3

A polymer was synthesized in the same manner as in Example 1, except for using 92.0 mol % of HPMA, 1.0 mol % of DM, and 7.0 mol % of DEG. The DM unit content and the ethylene oxide chain content in the polymer (hereinafter referred to as DPM921) thus obtained were respectively 1 mol % and 4.2 wt %. The weight average molecular weight determined by GPC was $3.0 \times 10^5$ and the content of the polymer having a weight average molecular weight of 10,000 or less was 2 wt %.

A filter material was prepared, and the elution test and blood evaluation were carried out in the same manner as in Example 1 to find that, in the filter material before sterilization treatment, the weight of polymer per unit surface area was 197 mg/m$^2$, the weight change was 0.5%, the leukocyte removal capability was 2.5, and the platelet recovery rate was 77%. In the filter material after autoclave sterilization, the weight change was 0.4%, the leukocyte removal capability was 2.8, and the platelet recovery rate was 73%.

Comparative Example 4

A polymer was synthesized in the same manner as in Example 10, except for using 83.0 mol % of HPMA, 10.0 mol % of DM, and 7.0 mol % of DEG. The DM unit content and the ethylene oxide chain content in the polymer (hereinafter referred to as DPM8310) thus obtained were respectively 10 mol % and 4.1 wt %. The weight average molecular weight determined by GPC was $3.1 \times 10^5$ and the content of the polymer having a weight average molecular weight of 10,000 or less was 2 wt %.

A filter material was prepared, and the elution test and blood evaluation were carried out in the same manner as in Example 1 to find that, in the filter material before sterilization treatment, the weight of polymer per unit surface area was 200 mg/m$^2$, the weight change was 10.2%, the leukocyte removal capability was 3.6, and the platelet recovery rate was 62%. In the filter material after autoclave sterilization, the weight change was 9.6%, the leukocyte removal capability was 3.7, and the platelet recovery rate was 59%.

Comparative Example 5

A polymer was synthesized in the same manner as in Example 1, except for using 80.0 mol % of HPMA, 3.0 mol % of DM, and 17.0 mol % of methoxyethylene glycol methacrylate with one ethylene oxide repetition in the ethylene oxide chain (hereinafter referred to as MEG). The DM unit content and the ethylene oxide chain content in the polymer (hereinafter referred to as MPM803) thus obtained were respectively 3 mol % and 5.2 wt %. The weight average molecular weight determined by GPC was $2.8 \times 10^5$ and the content of the polymer having a weight average molecular weight of 10,000 or less was 2 wt %.

A filter material was prepared, and the elution test and blood evaluation were carried out in the same manner as in Example 1 to find that, in the filter material before sterilization treatment, the weight of polymer per unit surface area was 201 mg/m$^2$, the weight change was 0.2%, the leukocyte removal capability was 3.4, and the platelet recovery rate was 73%. In the filter material after autoclave sterilization, the weight change was 0.2%, the leukocyte removal capability was 3.7, and the platelet recovery rate was 50%.

Comparative Example 6

A polymer was synthesized in the same manner as in Example 1, except for using 96.0 mol % of HPMA, 3.0 mol % of DM, and 1.0 mol % of methoxypolyethylene glycol methacrylate with 23 ethylene oxide repetitions in the ethylene oxide chain (hereinafter referred to as PEG). The DM unit content and the ethylene oxide chain content in the polymer (hereinafter referred to as PPM963) thus obtained were respectively 3 mol % and 6.6 wt %. The weight average molecular weight determined by GPC was $3.2 \times 10^5$ and the content of the polymer having a weight average molecular weight of 10,000 or less was 2 wt %.

A filter material was prepared, and the elution test and blood evaluation were carried out in the same manner as in Example 1 to find that, in the filter material before sterilization treatment, the weight of polymer per unit surface area was 205 mg/m$^2$, the weight change was 26.3%, the leukocyte removal capability was 2.6, and the platelet recovery rate was 85%. In the filter material after autoclave sterilization, the weight change was 25.1%, the leukocyte removal capability was 2.7, and the platelet recovery rate was 84%.

Comparative Example 7

A polymer was synthesized in the same manner as in Example 1, except for using 47.0 mol % of HPMA, 8.0 mol % of DM, and 45.0 mol % of NEG. The DM unit content and the ethylene oxide chain content in the polymer (hereinafter referred to as NPM478) thus obtained were respectively 8 mol % and 58.7 wt %. The weight average molecular weight determined by GPC was $3.5 \times 10^5$ and the content of the polymer having a weight average molecular weight of 10,000 or less was 2 wt %. 1.0 g of NPM478 was dissolved in 100 g of a mixed solvent of isopropanol and purified water. A nonwoven fabric made from polyethylene terephthalate was immersed in the solution. After removing excessive liquid, the nonwoven fabric was dried at room temperature for 16 hours to obtain the target filter material. The weight of polymer was 25 mg/m$^2$ per unit surface area.

The filter material was sterilized, and the elution test and blood evaluation were carried out in the same manner as in Example 1 to find that, in the filter material before sterilization treatment, the weight change was 43.6%, the leukocyte removal capability was 2.4, and the platelet recovery rate was 58%. In the filter material after autoclave sterilization, the weight change was 41.8%, the leukocyte removal capability was 2.5, and the platelet recovery rate was 56%.

Comparative Example 8

A polymer was synthesized in the same manner as in Example 1, except for using 75.0 mol % of HPMA, 5.0 mol % of DM, 20.0 mol % of DEG, 330 g of ethanol, and 0.78 g of V-65. The DM unit content and the ethylene oxide chain content in the polymer (hereinafter referred to as DPM755L) thus obtained were respectively 5 mol % and 11.5 wt %. The weight average molecular weight determined by GPC was $1.5 \times 10^5$ and the content of the polymer having a weight average molecular weight of 10,000 or less was 4 wt %.

A filter material was prepared, and the elution test and blood evaluation were carried out in the same manner as in Example 1 to find that, in the filter material before sterilization treatment, the weight of polymer per unit surface area was 200 mg/m$^2$, the weight change was 13.7%, the leukocyte removal capability was 3.4, and the platelet recovery rate was 81%. In the filter material after autoclave sterilization, the weight change was 13.3%, the leukocyte removal capability was 3.5, and the platelet recovery rate was 80%.

Comparative Example 9

A polymer was synthesized in the same manner as in Example 1, except for using monomers with a molar ratio of 75.0 mol % of HPMA, 5.0 mol % of DM, and 20.0 mol % of DEG, a monomer dropping time of 90 minutes, and 0.50 g of V-65. The DM unit content and the ethylene oxide chain content in the polymer (hereinafter referred to as DPM755H) thus obtained were respectively 5 mol % and 11.5 wt %. The weight average molecular weight determined by GPC was $4.6 \times 10^5$ and the content of the polymer having a weight average molecular weight of 10,000 or less was 2 wt %.

A filter material was prepared, and the elution test and blood evaluation were carried out in the same manner as in Example 1 to find that, in the filter material before sterilization treatment, the weight of polymer per unit surface area was 208 mg/m$^2$, the weight change was 10.0%, the leukocyte removal capability was 3.5, and the platelet recovery rate was 81%. In the filter material after autoclave sterilization, the weight change was 9.8%, the leukocyte removal capability was 3.5, and the platelet recovery rate was 79%.

Comparative Example 10

A polymer was synthesized in the same manner as in Example 1, except for using monomers with a molar ratio of 94.0 mol % of HPMA, 5.0 mol % of DM, and 1.0 mol % of DEG, a monomer dropping time of 90 minutes, and 0.50 g of V-65. The DM unit content and the ethylene oxide chain content in the polymer (hereinafter referred to as DPM945) thus obtained were respectively 5 mol % and 0.6 wt %. The weight average molecular weight determined by GPC was $4.8 \times 10^5$ and the content of the polymer having a weight average molecular weight of 10,000 or less was 2 wt %.

A filter material was prepared, and the elution test and blood evaluation were carried out in the same manner as in Example 1 to find that, in the filter material before sterilization treatment, the weight of polymer per unit surface area was 211 mg/m$^2$, the weight change was 0.2%, the leukocyte removal capability was 3.6, and the platelet recovery rate was 82%. In the filter material after autoclave sterilization, the weight change was 0.2%, the leukocyte removal capability was 3.6, and the platelet recovery rate was 63%.

TABLE 1

| | Polymer | Weight average molecular weight ($\times 10^4$) | Ethylene oxide chain content (wt %) | EO/Mw ($\times 10^{-8}$) | Sterilization treatment | Weight change (%) | Leukocyte removal capability (−Log) | Platelet recovery rate (%) |
|---|---|---|---|---|---|---|---|---|
| Example 1 | DPM943 | 31 | 1.8 | 5.8 | Not sterilized | 0.2 | 3.6 | 84 |
| | | | | | AC | 0.2 | 3.8 | 81 |
| Example 2 | DPM903 | 29 | 4.2 | 14.5 | Not sterilized | 1 | 3.7 | 86 |
| | | | | | AC | 0.8 | 4.0 | 84 |
| | | | | | γ-Rays | 1 | 3.8 | 86 |
| Example 3 | DPM863 | 32 | 6.5 | 20.3 | Not sterilized | 1.5 | 3.8 | 87 |
| | | | | | AC | 1.4 | 3.9 | 86 |
| Example 4 | DPM823 | 33 | 8.7 | 26.4 | Not sterilized | 2.9 | 3.5 | 88 |
| | | | | | AC | 2.6 | 3.7 | 88 |
| Example 5 | DPM885 | 30 | 4.2 | 14.0 | Not sterilized | 2.5 | 3.8 | 85 |
| | | | | | AC | 2.3 | 4.0 | 83 |
| Example 6 | DPM867 | 29 | 4.2 | 14.5 | Not sterilized | 2.8 | 3.9 | 84 |
| | | | | | AC | 2.5 | 4.0 | 83 |
| Example 7 | TPM943 | 32 | 3.6 | 11.3 | Not sterilized | 1.5 | 3.5 | 87 |
| | | | | | AC | 1.3 | 3.7 | 85 |
| Example 8 | NPM953 | 34 | 5.2 | 15.3 | Not sterilized | 2.3 | 3.5 | 88 |
| | | | | | AC | 2.1 | 3.6 | 87 |
| Example 9 | DBM873 | 30 | 5.5 | 18.3 | Not sterilized | 0.7 | 3.7 | 83 |
| | | | | | AC | 0.7 | 3.9 | 80 |
| Example 10 | DPM805L | 13 | 8.7 | 66.9 | Not sterilized | 4.7 | 3.8 | 85 |
| | | | | | AC | 4.3 | 3.8 | 84 |
| Example 11 | DPM805H | 44 | 8.7 | 19.8 | Not sterilized | 2.0 | 3.9 | 84 |
| | | | | | AC | 1.7 | 4.0 | 82 |
| Example 12 | DPM823H | 55 | 8.7 | 15.8 | Not sterilized | 1.8 | 3.6 | 87 |
| | | | | | AC | 1.5 | 3.7 | 82 |

TABLE 1-continued

| | Polymer | Weight average molecular weight (×10⁴) | Ethylene oxide chain content (wt %) | EO/Mw (×10⁻⁸) | Sterilization treatment | Weight change (%) | Leukocyte removal capability (−Log) | Platelet recovery rate (%) |
|---|---|---|---|---|---|---|---|---|
| Example 13 | DPM885L | 14 | 4.2 | 30.0 | Not sterilized | 2.8 | 3.7 | 88 |
| | | | | | AC | 2.6 | 3.9 | 88 |
| Example 14 | DPM943L | 8 | 1.8 | 22.5 | Not sterilized | 4.5 | 3.6 | 84 |
| | | | | | AC | 4.2 | 3.7 | 83 |
| Example 15 | DPM935 | 45 | 1.2 | 2.7 | Not sterilized | 0.1 | 3.7 | 84 |
| | | | | | AC | 0.1 | 3.8 | 80 |
| Comparative Example 1 | DPM973 | 28 | 0 | 0.0 | Not sterilized | 0.1 | 3.5 | 80 |
| | | | | | AC | 0.1 | 3.8 | 65 |
| Comparative Example 2 | DPM753 | 30 | 12.6 | 42.0 | Not sterilized | 11.4 | 3.3 | 82 |
| | | | | | AC | 10.9 | 3.4 | 82 |
| Comparative Example 3 | DPM921 | 30 | 4.2 | 14.0 | Not sterilized | 0.5 | 2.5 | 77 |
| | | | | | AC | 0.4 | 2.8 | 73 |
| Comparative Example 4 | DPM8310 | 31 | 4.1 | 13.2 | Not sterilized | 10.2 | 3.6 | 62 |
| | | | | | AC | 9.6 | 3.7 | 59 |
| Comparative Example 5 | MPM803 | 28 | 5.2 | 18.6 | Not sterilized | 0.2 | 3.4 | 73 |
| | | | | | AC | 0.2 | 3.7 | 50 |
| Comparative Example 6 | PPM963 | 32 | 6.6 | 20.6 | Not sterilized | 26.3 | 2.6 | 85 |
| | | | | | AC | 25.1 | 2.7 | 84 |
| Comparative Example 7 | NPM478 | 35 | 58.7 | 168 | Not sterilized | 43.6 | 2.4 | 58 |
| | | | | | AC | 41.8 | 2.5 | 56 |
| Comparative Example 8 | DPM755L | 15 | 11.5 | 76.7 | Not sterilized | 13.7 | 3.4 | 81 |
| | | | | | AC | 13.3 | 3.5 | 80 |
| Comparative Example 9 | DPM755H | 46 | 11.5 | 25.0 | Not sterilized | 10.0 | 3.5 | 81 |
| | | | | | AC | 9.8 | 3.5 | 79 |
| Comparative Example 10 | DPM945 | 48 | 0.6 | 1.3 | Not sterilized | 0.2 | 3.6 | 82 |
| | | | | | AC | 0.2 | 3.6 | 63 |

DPM = DEG/HPMA/DM
TPM = TEG/HPMA/DM
NPM = NEG/HPMA/DM
DBM = DEG/HBMA/DM
MPM = MEG/HPMA/DM
PPM = PEG (n = 23)/HPMA/DM
AC: Autoclave sterilization

INDUSTRIAL APPLICABILITY

The filter for selectively removing leukocytes of the present invention is highly safe and exhibits outstanding blood processing performance. Specifically, the filter elutes only a slight amount of polymer, causes only a very slight amount of platelets to adhere during use, and can capture and remove leukocytes at a high yield. In addition, due to incorporation of a small amount of an ethylene oxide chain, the filter is provided with outstandingly superior sterilization resistance, with almost no change and deterioration of elution properties and blood processing performance after sterilization treatment. The filter of the present invention is particularly useful for selectively removing leukocytes in human whole blood, and also extremely useful as a filter for platelet transfusion and extra corporeal circulation of blood for leukocyte removal.

The invention claimed is:

1. A filter material for selectively removing leukocytes with excellent sterilization resistance comprising a polymer on the surface of a filter base material, wherein the polymer is formed from a hydroxyalkyl (meth)acrylate unit with the alkyl moiety having 3 or 4 carbon atoms, a monomer unit having a basic nitrogen-containing functional group, and a monomer unit containing an ethylene oxide chain with 2-9 ethylene oxide repetitions, wherein the content of the monomer unit having a basic nitrogen-containing functional group in the polymer is 2-9 mol % and the content of the ethylene oxide chain in the polymer is 1-10 wt %.

2. The filter material according to claim 1, wherein the polymer is a vinyl-type polymer.

3. The filter material according to claim 1, wherein the hydroxyalkyl (meth)acrylate unit is hydroxypropyl methacrylate.

4. The filter material according to claim 1, wherein the number of ethylene oxide repetitions in the ethylene oxide chain is 2.

5. The filter material according to claim 1, wherein the weight average molecular weight of the polymer is 100,000-500,000 and the content of the polymer having a weight average molecular weight of 10,000 or less is less than 10 wt %.

6. The filter material according to claim 1, wherein the ratio of the content of the ethylene oxide chain in the polymer to the weight average molecular weight of the polymer is from $3.5 \times 10^{-6}$ to $40 \times 10^{-6}$.

7. The filter material according to claim 1, wherein the amount of the polymer introduced per unit surface area of the filter base material is 90-300 mg/m².

8. The filter material according to claim 1, which is used for selectively removing leukocytes from human whole blood.

9. The filter material according to claim 2, wherein the hydroxyalkyl (meth)acrylate unit is hydroxypropyl methacrylate.

10. A filter material for selectively removing leukocytes with excellent sterilization resistance, comprising:
a polymer on the surface of a filter base material, wherein the polymer is formed from a hydroxyalkyl (meth)acrylate unit with the alkyl moiety having 3 or 4 carbon atoms, a monomer unit having a basic nitrogen-containing functional group, and a monomer unit containing an ethylene oxide chain with 2-9 ethylene oxide repetitions;

wherein the content of the monomer unit having a basic nitrogen-containing functional group in the polymer is 2-9 mol % and the content of the ethylene oxide chain in the polymer is 1-10 wt %;

wherein the weight average molecular weight of the polymer is 100,000-500,000 and the content of the polymer having a weight average molecular weight of 10,000 or less is less than 10 wt %; and wherein the amount of the polymer introduced per unit surface area of the filter base material is 90-300 mg/m$^2$.

11. The filter material according to claim 10, wherein the polymer is a vinyl-type polymer.

12. The filter material according to claim 10, wherein the hydroxyalkyl (meth)acrylate unit is hydroxypropyl methacrylate.

13. The filter material according to claim 11, wherein the hydroxyalkyl (meth)acrylate unit is hydroxypropyl methacrylate.

14. The filter material according to claim 10, wherein the number of ethylene oxide repetitions in the ethylene oxide chain is 2.

15. The filter material according to claim 11, wherein the number of ethylene oxide repetitions in the ethylene oxide chain is 2.

* * * * *